(12) United States Patent
Cicic

(10) Patent No.: US 11,292,835 B2
(45) Date of Patent: Apr. 5, 2022

(54) LOW DOSE ANTIBODY-BASED METHODS FOR TREATING HEMATOLOGIC MALIGNANCIES

(71) Applicant: Actinium Pharmaceuticals, Inc., New York, NY (US)

(72) Inventor: Dragan Cicic, Brooklyn, NY (US)

(73) Assignee: Actinium Pharmaceuticals, Inc., New York, NY (US)

(*) Notice: Subject to any disclaimer, the term of this patent is extended or adjusted under 35 U.S.C. 154(b) by 301 days.

(21) Appl. No.: 16/300,672

(22) PCT Filed: May 25, 2017

(86) PCT No.: PCT/US2017/034406
§ 371 (c)(1),
(2) Date: Nov. 12, 2018

(87) PCT Pub. No.: WO2017/205587
PCT Pub. Date: Nov. 30, 2017

(65) Prior Publication Data
US 2019/0263903 A1   Aug. 29, 2019

Related U.S. Application Data

(60) Provisional application No. 62/342,568, filed on May 27, 2016.

(51) Int. Cl.
| | | |
|---|---|---|
| C07K 16/28 | (2006.01) | |
| A61K 47/68 | (2017.01) | |
| A61P 35/02 | (2006.01) | |
| A61K 51/10 | (2006.01) | |
| A61K 39/00 | (2006.01) | |

(52) U.S. Cl.
CPC ...... *C07K 16/2803* (2013.01); *A61K 47/6803* (2017.08); *A61K 51/1069* (2013.01); *A61K 51/1093* (2013.01); *A61K 51/1096* (2013.01); *A61P 35/02* (2018.01); *A61K 2039/505* (2013.01)

(58) Field of Classification Search
CPC ............ C07K 16/2803; C07K 16/2896; A61K 47/6803; A61K 47/6801; A61K 51/1093; A61K 47/6887; A61K 51/1096; A61K 51/1027; A61K 51/1045; A61K 51/1069; A61K 51/10; A61K 2039/505; A61K 2121/00; A61P 35/02; A61P 35/00
See application file for complete search history.

(56) References Cited

U.S. PATENT DOCUMENTS 4,923,985 A   5/1990   Gansow et al.
6,683,162 B2 * 1/2004   Scheinberg ............. A61P 35/00
                                                534/11

OTHER PUBLICATIONS

Jurcic, J. G., et al. "Targeted alpha-particle nano-generator actinium-225 (225Ac)-lintuzumab (anti-CD33) in acute myeloid leukemia (AML)." Clinical Lymphoma, Myeloma and Leukemia 13 (2013): S379-S380. (Year: 2013).*
Jurcic, Joseph G., et al. "Phase I trial of the targeted alpha-particle nano-generator actinium-225 (225Ac)-lintuzumab (anti-CD33) in combination with low-dose cytarabine (LDAC) for older patients with untreated acute myeloid leukemia (AML)." Blood (2013) 122(21): 1460-1460 (Year: 2013).*
Rosenblat, Todd L., et al. "Sequential cytarabine and a-particle immunotherapy with bismuth-213-lintuzumab (HuM195) for acute myeloid leukemia." Clinical Cancer Research 16.21 (2010): 5303-5311. (Year: 2010).*
Burnett, Alan K., et al. "A comparison of low-dose cytarabine and hydroxyurea with or without all-trans retinoic acid for acute myeloid leukemia and high-risk myelodysplastic syndrome in patients not considered fit for intensive treatment." Cancer 109.6 (2007): 1114-1124 (Year: 2007).*
Topp, Max S., et al. "Targeted therapy with the T-cell-engaging antibody blinatumomab of chemotherapy-refractory minimal residual disease in B-lineage acute lymphoblastic leukemia patients results in high response rate and prolonged leukemia-free survival." J Clin Oncol 29.18 (2011): 2493-2498. (Year: 2011).*
Zhu, Min, et al. "Blinatumomab, a bispecific T-cell engager (BiTE®) for CD-19 targeted cancer immunotherapy: clinical pharmacology and its implications." Clinical pharmacokinetics 55.10 (2016): 1271-1288. (Year: 2016).*
Walter et al., Blood, 2012, vol. 119, pp. 6198-6208 (Year: 2012).*
Dutta and Saxena, Indian Journal of Hematology and Blood Transfusion, 2014, vol. 30, pp. 130-134 (Year: 2014).*
Krause et al. Nature Medicine, 2013, vol. 19, pp. 1513-1517 (Year: 2013).*
Caron et al., Blood, 1994, vol. 83, pp. 1760-1768 (Year: 1994).*
Deng et al., Expert Opinion on Drug Metabolism and Toxicology, 2012, vol. 8, pp. 141-160 (Year: 2012).*
Maguire et al (Journal of Nuclear Medicine, 2014, vol. 55, pp. 1492-1498) (Year: 2014).*
Co, et al., "Chimeric and humanized antibodies with specificity for the CD33 antigen.", J. Immunol. 148:1149-1154, 1992.

(Continued)

*Primary Examiner* — Karen A. Canella
(74) *Attorney, Agent, or Firm* — Alan J. Morrison

(57) ABSTRACT

This invention provides a method for treating a subject afflicted with a hematologic malignancy comprising administering to the subject an agent targeting a hematologic malignancy-associated antigen, wherein the subject has a low peripheral cancerous cell burden. This invention also provides a method for treating a subject afflicted with a hematologic malignancy and having a high peripheral cancerous cell burden, comprising (i) medically lowering the subject's peripheral cancerous cell burden, and (ii) while the subject's peripheral cancerous cell burden is still low, administering to the subject an agent targeting a hematologic malignancy-associated antigen. Particularly envisioned are the subject methods for treating acute myeloid leukemia using an anti-CD33 antibody labeled with an alpha-emitting isotope, such as $^{225}$Ac-HuM195.

6 Claims, 7 Drawing Sheets

Specification includes a Sequence Listing.

(56) References Cited

OTHER PUBLICATIONS

Harousseau, et al., "Arandomized phase 3 study of tipifarnib compared with best supportive care, including hydroxyurea, in the treatment of newly diagnosed acute myeloid leukemia in patients 70 years or older", Blood, Aug. 6, 2009, vol. 114, No. 6, 1166-1173.
Jurcic, et al., "Phase I Trial of Targeted Alpha-Particle Therapy with Actinium-225 (225Ac)-Lintuzumab and Low-Dose Cytarabine (LDAC) in Patients Age 60 or Older with Untreated Acute Myeloid Leukemia (AML)", The American Society of Hematology, Abstract, vol. 128, Issue 22, Dec. 2, 2016, 7 pgs.
Kumar, "Genetic Abnormalities and Challenges in the Treatment of Acute Myeloid Leukemia", Genes & Cancer, vol. 2, No. 2, 95-107, 2011.
McDevitt, et al., "Design and synthesis of 225Ac radioimmunopharmaceuticals", Applied Radiation and Isotopes, 57 (2002) 841-847.
Mulford et al., "The Promise of Targeted α-Particle Therapy", The Journal of Nuclear Medicine, vol. 46, No. 1 (Suppl), Jan. 2005, 199S-204S.
Pollard, et al., "Correlation of CD33 expression level with disease characteristics and response to gemtuzumab ozogamicin containing chemotherapy in childhood AML", Blood, Apr. 19, 2012, 119(16):3705-3711.
SWOG Oncology Research Professional (ORP) Manual, vol. I, Chapter 11A, Leukemia (2014).
V.H.J. van der Velden, et al., "High CD33-antigen loads in peripheral blood limit the efficacy of gemtuzumab ozogamicin (Mylotarg) treatment in acute myeloid leukemia patients", Leukemia, 2004, May 18(5):983-988.
De Kruijff, et al., "A Critical Review of Alpha Radionuclide Therapy—How to Deal with Recoiling Daughters?", Pharmaceuticals, Jun. 2015, ISSN 1424-8247, 321-336.

\* cited by examiner

```
624 TCTAGACCACCATGGAGAAAGACACACTCCTGCTATGGGTCCTACTTCTCTGGGTTCCAGGTTCCACAGGTGACATTCAG
      M  E  K  D  T  L  L  L  W  V  L  L  W  V  P  G  S  T  G  D  I  Q
704 ATGACCCAGTCTCCGAGCTCTCTGTCCGCATCAGTAGGAGACAGGGTCACCATCACATGCAGAGCCAGCGAAAGTGTCGA
       M  T  Q  S  P  S  S  L  S  A  S  V  G  D  R  V  T  I  T  C  R  A  S  E  S  V  D
784 CAATTATGGCATTAGCTTTATGAACTGGTTCCAACAGAAACCCGGGAAGGCTCCTAAGCTTCTGATTTACGCTGCATCCA
        N  Y  G  I  S  F  M  N  W  F  Q  Q  K  P  G  K  A  P  K  L  L  I  Y  A  A  S
864 ACCAAGGCTCCGGGGTACCCTCTCGCTTCTCAGGCAGTGGATCTGGGACAGACTTCACTCTCACCATTTCATCTCTGCAG
       N  Q  G  S  G  V  P  S  R  F  S  G  S  G  S  G  T  D  F  T  L  T  I  S  S  L  Q
944 CCTGATGACTTCGCAACCTATTACTGTCAGCAAAGTAAGGAGGTTCCGTGGACGTTCGGTCAAGGGACCAAGGTGGAGAT
        P  D  D  F  A  T  Y  Y  C  Q  Q  S  K  E  V  P  W  T  F  G  Q  G  T  K  V  E  I
1024 CAAACGTAAGTAGAATCCAAAGTCTAGAAATTCTAAACTCTGAGGGGGTCGGATGACGTGGCCATTCTTTGCCTAAAGCA
        K  R
1104 TTGAGTTTACTGCAAGGTCAGAAAAGCATGCAAAGCCCTCAGAATGGCTGCAAAGAGCTCCAACAAAACAATTTAGAACT

1184 TTATTAAGGAATAGGGGGAAGCTAGGAAGAAACTCAAAACATCAAGATTTTAAATACGCTTCTTGGTCTCCTTGCTATAA

1264 TTATCTGGGATAAGCATGCTGTTTTCTGTCTGTCCCTAACATGCTCTGTGATTATCCGCAAACAACACACCCAAGGGCAG

1344 AACTTTGTTACTTAAACACCATCCTGTTTGCTTCTTTCCTCAGGAACTGTGGCTGCACCATCTGTCTTCATCTTCCCGCC
                                                         T  V  A  A  P  S  V  F  I  F  P  P
1424 ATCTGATGAGCAGTTGAAATCTGGAACTGCCTCTGTTGTGTGCCTGCTGAATAACTTCTATCCCAGAGAGGCCAAAGTAC
       S  D  E  Q  L  K  S  G  T  A  S  V  V  C  L  L  N  N  F  Y  P  R  E  A  K  V
1504 AGTGGAAGGTGGATAACGCCCTCCAATCGGGTAACTCCCAGGAGAGTGTCACAGAGCAGGACAGCAAGGACAGCACCTAC
       Q  W  K  V  D  N  A  L  Q  S  G  N  S  Q  E  S  V  T  E  Q  D  S  K  D  S  T  Y
1584 AGCCTCAGCAGCACCCTGACGCTGAGCAAAGCAGACTACGAGAAACACAAAGTCTACGCCTGCGAAGTCACCCATCAGGG
        S  L  S  S  T  L  T  L  S  K  A  D  Y  E  K  H  K  V  Y  A  C  E  V  T  H  Q  G
1664 CCTGAGCTCGCCCGTCACAAAGAGCTTCAACAGGGGAGAGTGTTAGAGGGAGAAGTGCCCCACCTGCTCCTCAGTTCCA
       L  S  S  P  V  T  K  S  F  N  R  G  E  C  •
1744 GCCTGACCCCCTCCCATCCTTTGGCCTCTGACCCTTTTTCCACAGGGGACCTACCCCTATTGCGGTCCTCCAGCTCATCT

1824 TTCACCTCACCCCCCTCCTCCTCCTTGGCTTTAATTATGCTAATGTTGGAGGAGAATGAATAAATAAAGTGAATCTTTGC

1904 ACCTGTGGTTTCTCTCTTTCCTCATTTAATAATTATTATCTGTTGTTTTACCAACTACTCAATTTCTCTTATAAGGGACT

1984 AAATATGTAGTCATCCTAAGGCGCATAACCATTTATAAAAATCATCCTTCATTCTATTTTACCCTATCATCCTCTGCAAG

2064 ACAGTCCTCCCTCAAACCCACAAGCCTTCTGTCCTCACAGTCCCCTGGGCCATGGTAGGAGAGACTTGCTTCCTTGTTTT

2144 CCCCTCCTCAGCAAGCCCTCATAGTCCTTTTTAAGGGTGACAGGTCTTACAGTCATATATCCTTTGATTCAATTCCCTGA

2224 GAATCAACCAAAGCAAATTTTTCAAAAGAAGAAACCTGCTATAAAGAGAATCATTCATTGCAACATGATATAAAATAACA

2304 ACACAATAAAAGCAATTAAATAAACAAACAATAGGGAAATGTTTAAGTTCATCATGGTACTTAGACTTAATGGAATGTCA

2384 TGCCTTATTTACATTTTTAAACAGGTACTGAGGGACTCCTGTCTGCCAAGGGCCGTATTGAGTACTTTCCACAACCTAAT

2464 TTAATCCACACTATACTGTGAGATTAAAAACATTCATTAAAATGTTGCAAAGGTTCTATAAAGCTGAGAGACAAATATAT

2544 TCTATAACTCAGCAATCCCACTTCTAGGATCC
```

Figure 2

```
 624 TCTAGACCACCATGGGATGGAGCTGGATCTTTCTCTTCCTCCTGTCAGGAACTGCTGGCGTCCACTCTCAGGTTCAGCTG
                  M  G  W  S  W  I  F  L  F  L  L  S  G  T  A  G  V  H  S  Q  V  Q  L
 704 GTGCAGTCTGGAGCTGAGGTGAAGAAGCCTGGGAGCTCAGTGAAGGTTTCCTGCAAAGCTTCTGGCTACACCTTCACTGA
      V  Q  S  G  A  E  V  K  K  P  G  S  S  V  K  V  S  C  K  A  S  G  Y  T  F  T  D
 784 CTACAACATGCACTGGGTGAGGCAGGCTCCTGGCCAAGGCCTGGAATGGATTGGATATATTTATCCTTACAATGGTGGTA
       Y  N  M  H  W  V  R  Q  A  P  G  Q  G  L  E  W  I  G  Y  I  Y  P  Y  N  G  G
 864 CCGGCTACAACCAGAAGTTCAAGAGCAAGGCCACAATTACAGCAGACGAGAGTACTAACACAGCCTACATGGAACTCTCC
     T  G  Y  N  Q  K  F  K  S  K  A  T  I  T  A  D  E  S  T  N  T  A  Y  M  E  L  S
 944 AGCCTGAGGTCTGAGGACACTGCAGTCTATTACTGCGCAAGAGGGCGCCCCGCTATGGACTACTGGGGCCAAGGGACTCT
      S  L  R  S  E  D  T  A  V  Y  Y  C  A  R  G  R  P  A  M  D  Y  W  G  Q  G  T  L
1024 GGTCACTGTCTCTTCAGGTAAGAATGGCCTCTAGACCACCATGGGATGGAGCTTTCTGGGGCAGGCCAGGCCTGACCTTG
      V  T  V  S  S
1104 GCTTTGGGGCAGGGAGGGGGCTAAGGTGAGGCAGGTGGCGCCAGCCAGGTGCACACCCAATGCCCATGAGCCCAGACACT

1184 GGACGCTGAACCTCGCGGACAGTTAAGAACCCAGGGGCCTCTGCGCCCTGGGCCCAGCTCTGTCCCACACCGCGGTCACA

1264 TGGCACCACCTCTCTTGCAGCCTCCACCAAGGGCCCATCGGTCTTCCCCCTGGCACCCTCCTCCAAGAGCACCTCTGGGG
                            A  S  T  K  G  P  S  V  F  P  L  A  P  S  S  K  S  T  S  G
1344 GCACAGCGGCCCTGGGCTGCCTGGTCAAGGACTACTTCCCCGAACCGGTGACGGTGTCGTGGAACTCAGGCGCCCTGACC
      G  T  A  A  L  G  C  L  V  K  D  Y  F  P  E  P  V  T  V  S  W  N  S  G  A  L  T
1424 AGCGGCGTGCACACCTTCCCGGCTGTCCTACAGTCCTCAGGACTCTACTCCCTCAGCAGCGTGGTGACCGTGCCCTCCAG
       S  G  V  H  T  F  P  A  V  L  Q  S  S  G  L  Y  S  L  S  S  V  V  T  V  P  S  S
1504 CAGCTTGGGCACCCAGACCTACATCTGCAACGTGAATCACAAGCCCAGCAACACCAAGGTGGACAAGAAAGTTGGTGAGA
       S  L  G  T  Q  T  Y  I  C  N  V  N  H  K  P  S  N  T  K  V  D  K  K  V
1584 GGCCAGCACAGGGAGGGAGGGTGTCTGCTGGAAGCCAGGCTCAGCGCTCCTGCCTGGACGCATCCCGGCTATGCAGCCCC

1664 AGTCCAGGGCAGCAAGGCAGGCCCCGTCTGCCTCTTCACCCGGAGGCCTCTGCCCGCCCCACTCATGCTCAGGGAGAGGG

1744 TCTTCTGGCTTTTTCCCCAGGCTCTGGGCAGGCACAGGCTAGGTGCCCCTAACCCAGGCCCTGCACACAAAGGGGCAGGT

1824 GCTGGGCTCAGACCTGCCAAGAGCCATATCCGGGAGGACCCTGCCCCTGACCTAAGCCCACCCCAAAGGCCAAACTCTCC

1904 ACTCCCTCAGCTCGGACACCTTCTCTCCTCCCAGATTCCAGTAACTCCCAATCTTCTCTCTGCAGAGCCCAAATCTTGTG
                                                                          E  P  K  S  C
1984 ACAAAACTCACACATGCCCACCGTGCCCAGGTAAGCCAGCCCAGGCCTCGCCCTCCAGCTCAAGGCGGGACAGGTGCCCT
      D  K  T  H  T  C  P  P  C  P
2064 AGAGTAGCCTGCATCCAGGGACAGGCCCCAGCCGGGTGCTGACACGTCCACCTCCATCTCTTCCTCAGCACCTGAACTCC
                                                                             A  P  E  L
2144 TGGGGGGACCGTCAGTCTTCCTCTTCCCCCCAAAACCCAAGGACACCCTCATGATCTCCCGGACCCCTGAGGTCACATGC
      L  G  G  P  S  V  F  L  F  P  P  K  P  K  D  T  L  M  I  S  R  T  P  E  V  T  C
2224 GTGGTGGTGGACGTGAGCCACGAAGACCCTGAGGTCAAGTTCAACTGGTACGTGGACGGCGTGGAGGTGCATAATGCCAA
      V  V  V  D  V  S  H  E  D  P  E  V  K  F  N  W  Y  V  D  G  V  E  V  H  N  A  K
2304 GACAAAGCCGCGGGAGGAGCAGTACAACAGCACGTACCGTGTGGTCAGCGTCCTCACCGTCCTGCACCAGGACTGGCTGA
       T  K  P  R  E  E  Q  Y  N  S  T  Y  R  V  V  S  V  L  T  V  L  H  Q  D  W  L
2384 ATGGCAAGGAGTACAAGTGCAAGGTCTCCAACAAAGCCCTCCCAGCCCCCATCGAGAAAACCATCTCCAAAGCCAAAGGT
      N  G  K  E  Y  K  C  K  V  S  N  K  A  L  P  A  P  I  E  K  T  I  S  K  A  K
2464 GGGACCCGTGGGGTGCGAGGGCCACATGGACAGAGGCCGGCTCGGCCCACCCTCTGCCCTGAGAGTGACCGCTGTACCAA
```

Figure 3

```
2544 CCTCTGTCCCTACAGGGCAGCCCCGAGAACCACAGGTGTACACCCTGCCCCCATCCCGGGATGAGCTGACCAAGAACCAG
            G  Q  P  R  E  P  Q  V  Y  T  L  P  P  S  R  D  E  L  T  K  N  Q
2624 GTCAGCCTGACCTGCCTGGTCAAAGGCTTCTATCCCAGCGACATCGCCGTGGAGTGGGAGAGCAATGGGCAGCCGGAGAA
       V  S  L  T  C  L  V  K  G  F  Y  P  S  D  I  A  V  E  W  E  S  N  G  Q  P  E  N
2704 CAACTACAAGACCACGCCTCCCGTGCTGGACTCCGACGGCTCCTTCTTCCTCTACAGCAAGCTCACCGTGGACAAGAGCA
       N  Y  K  T  T  P  P  V  L  D  S  D  G  S  F  F  L  Y  S  K  L  T  V  D  K  S
2784 GGTGGCAGCAGGGGAACGTCTTCTCATGCTCCGTGATGCATGAGGCTCTGCACAACCACTACACGCAGAAGAGCCTCTCC
       R  W  Q  Q  G  N  V  F  S  C  S  V  M  H  E  A  L  H  N  H  Y  T  Q  K  S  L  S
2864 CTGTCTCCGGGTAAATGAGTGCGACGGCCGGCAAGCCCCGCTCCCCGGGCTCTCGCGGTCGCACGAGGATGCTTGGCAC
       L  S  P  G  K  *
2944 GTACCCCTGTACATACTTCCCGGGCGCCCAGCATGGAAATAAAGCACCCAGCGCTGCCCTGGGCCCCTGCGAGACTGTG

3024 ATGGTTCTTTCCACGGGTCAGGCCGAGTCTGAGGCCTGAGTGGCATGAGGGAGGCAGAGCGGGTCCCACTGTCCCCACAC

3104 TGGCCCAGGCTGTGCAGGTGTGCCTGGGCCGCCTAGGGTGGGGCTCAGCCAGGGGCTGCCCTCGGCAGGGTGGGGGATTT

3184 GCCAGCGTGGCCCTCCCTCCAGCAGCACCTGCCCTGGGCTGGGCCACGGGAAGCCCTAGGAGCCCCTGGGGACAGACACA

3264 CAGCCCCTGCCTCTGTAGGAGACTGTCCTGTTCTGTGAGCGCCCTGTCCTCCGACCTCCATGCCCACTCGGGGGCATGCC

3344 TAGTCCATGTGCGTAGGGACAGGCCCTCCCTCACCCATCTACCCCCACGGCACTAACCCCTGGCTGCCCTGCCCAGCCTC

3424 GCACCCGCATGGGGACACAACCGACTCCGGGGACATGCACTCTCGGGCCCTGTGGAGGGACTGGTGCAGATGCCCACACA

3504 CACACTCAGCCCAGACCCGTTCAACAAACCCCGCACTGAGGTTGGCCGGCCACACGGCCACCACACACACGTGCACGC

3584 CTCACACACGGAGCCTCACCCGGGCGAACTGCACAGCACCCAGACCAGAGCAAGGTCCTCGCACACGTGAACACTCCTCG

3664 GACACAGGCCCCCACGAGCCCCACGCGGCACCTCAAGGCCCACGAGCCTCTCGGCAGCTTCTCCACATGCTGACCTGCTC

3744 AGACAAACCCAGCCCTCCTCTCACAAGGGTGCCCCTGCAGCCGCCACACACACACAGGGGATCACACACCACGTCACGTC

3824 CCTGGCCCTGGCCCACTTCCCAGTGCCGCCCTTCCCTGCAGGATCC
```

Figure 3
Continued

Protocol Schema

Phase I Dose Escalation Component (3+3 Design)

| Low Dose Ara-C (LDAC) 20 mg subQ q 12 hrs X 10D Cycle 1 | | Fractionated Doses | | LDAC Cycle 2-12 every 28 D beginning 4 weeks after dose 2 of Lintuzumab-Ac225 |
|---|---|---|---|---|
| | | Dose 1 | Dose 2 | |
| | | Lintuzmab-Ac225 | Lintuzmab-Ac225 | |
| D-10 | D-1 | D-14-17 | D-18-24 | |
| | | plus furosemide and spironolactone | | |

Phase II Component (Simon 2-stage Design)

| Low Dose Ara-C (LDAC) 20 mg subQ q12 hrs X 10D Cycle 1 | | MTD | | LDAC Cycle 2-12 every 28 D |
|---|---|---|---|---|
| | | Dose 1 | Dose 2 | |
| | | Lintuzmab-Ac225 | Lintuzmab-Ac225 | |
| D-10 | D-1 | D-14-17 | D-18-24 | |
| | | plus furosemide and spironolactone | | |

Dose Escalation Schedule

| Dose Level | Ac-225 Activity per fractionated dose (μCi/Kg) | Total Dose (μCi/Kg) | HuM195 per fractionated dose (μg/Kg) | Total HuM195 dose (μg/Kg) |
|---|---|---|---|---|
| 1 | 0.5 | 1.0 | 7.5 | 15 |
| 2 | 1 | 2 | 10 | 20 |
| 3 | 1.5 | 3 | 10 | 20 |
| 4 | 2 | 4 | 12.5 | 25 |

Statistics

Historical CR for this population = 20%

Target CR rate of 35% (p=.05, power = 80%)
Need 7 CRs in first 31 subjects to proceed to stage 2
Total sample size in the Phase II portion = up to 53 subjects

Primary endpoint: Response rate (CR + CRp)
Eligibility

Patients age ≥ 60 years with newly diagnosed AML with 20% blasts who decline or are considered unfit for intensive induction therapy because of poor risk factors or co-morbid conditions, or subjects ≥ 70 years old with newly diagnosed AML.

Figure 6

SEQUENCE LISTING

```
<160> NUMBER OF SEQ ID NOS: 4

<210> SEQ ID NO 1
<211> LENGTH: 1952
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (12)..(407)
<220> FEATURE:
<221> NAME/KEY: CDS
<222> LOCATION: (766)..(1083)

<400> SEQUENCE: 1
tctagaccac c atg gag aaa gac aca ctc ctg cta tgg gtc cta ctt ctc       50
            Met Glu Lys Asp Thr Leu Leu Leu Trp Val Leu Leu Leu
              1               5                  10 tgg gtt cca ggt tcc aca ggt gac att cag atg acc cag tct ccg agc       98
Trp Val Pro Gly Ser Thr Gly Asp Ile Gln Met Thr Gln Ser Pro Ser
     15                  20                  25 tct ctg tcc gca tca gta gga gac agg gtc acc atc aca tgc aga gcc      146
Ser Leu Ser Ala Ser Val Gly Asp Arg Val Thr Ile Thr Cys Arg Ala
 30                  35                  40                  45 agc gaa agt gtc gac aat tat ggc att agc ttt atg aac tgg ttc caa      194
Ser Glu Ser Val Asp Asn Tyr Gly Ile Ser Phe Met Asn Trp Phe Gln
                 50                  55                  60 cag aaa ccc ggg aag gct cct aag ctt ctg att tac gct gca tcc aac      242
Gln Lys Pro Gly Lys Ala Pro Lys Leu Leu Ile Tyr Ala Ala Ser Asn
             65                  70                  75 caa ggc tcc ggg gta ccc tct cgc ttc tca ggc agt gga tct ggg aca      290
Gln Gly Ser Gly Val Pro Ser Arg Phe Ser Gly Ser Gly Ser Gly Thr
         80                  85                  90 gac ttc act ctc acc att tca tct ctg cag cct gat gac ttc gca acc      338
Asp Phe Thr Leu Thr Ile Ser Ser Leu Gln Pro Asp Asp Phe Ala Thr
     95                 100                 105 tat tac tgt cag caa agt aag gag gtt ccg tgg acg ttc ggt caa ggg      386
Tyr Tyr Cys Gln Gln Ser Lys Glu Val Pro Trp Thr Phe Gly Gln Gly
110                 115                 120                 125 acc aag gtg gag atc aaa cgt aagtagaatc caaagtctag aaattctaaa         437
Thr Lys Val Glu Ile Lys Arg
                130 ctctgagggg gtcggatgac gtggccattc tttgcctaaa gcattgagtt tactgcaagg    497 tcagaaaagc atgcaaagcc ctcagaatgg ctgcaaagag ctccaacaaa acaatttaga    557 actttattaa ggaatagggg gaagctagga agaaactcaa aacatcaaga ttttaaatac    617 gcttcttggt ctccttgcta taattatctg ggataagcat gctgttttct gtctgtccct    677 aacatgctct gtgattatcc gcaaacaaca cacccaaggg cagaactttg ttacttaaac    737 accatcctgt ttgcttcttt cctcagga act gtg gct gca cca tct gtc ttc       789
                                Thr Val Ala Ala Pro Ser Val Phe
```

```
                                  135                 140
atc ttc ccg cca tct gat gag cag ttg aaa tct gga act gcc tct gtt    837
Ile Phe Pro Pro Ser Asp Glu Gln Leu Lys Ser Gly Thr Ala Ser Val
                145                 150                 155 gtg tgc ctg ctg aat aac ttc tat ccc aga gag gcc aaa gta cag tgg    885
Val Cys Leu Leu Asn Asn Phe Tyr Pro Arg Glu Ala Lys Val Gln Trp
            160                 165                 170 aag gtg gat aac gcc ctc caa tcg ggt aac tcc cag gag agt gtc aca    933
Lys Val Asp Asn Ala Leu Gln Ser Gly Asn Ser Gln Glu Ser Val Thr
        175                 180                 185 gag cag gac agc aag gac agc acc tac agc ctc agc agc acc ctg acg    981
Glu Gln Asp Ser Lys Asp Ser Thr Tyr Ser Leu Ser Ser Thr Leu Thr
    190                 195                 200 ctg agc aaa gca gac tac gag aaa cac aaa gtc tac gcc tgc gaa gtc    1029
Leu Ser Lys Ala Asp Tyr Glu Lys His Lys Val Tyr Ala Cys Glu Val
205                 210                 215                 220 acc cat cag ggc ctg agc tcg ccc gtc aca aag agc ttc aac agg gga    1077
Thr His Gln Gly Leu Ser Ser Pro Val Thr Lys Ser Phe Asn Arg Gly
                225                 230                 235 gag tgt tagagggaga agtgccccca cctgctcctc agttccagcc tgaccccctc     1133
Glu Cys ccatcctttg gcctctgacc cttttccac aggggaccta cccctattgc ggtcctccag   1193
ctcatctttc acctcacccc cctcctcctc cttggcttta attatgctaa tgttggagga   1253
gaatgaataa ataaagtgaa tctttgcacc tgtggtttct ctctttcctc atttaataat   1313
tattatctgt tgttttacca actactcaat ttctcttata agggactaaa tatgtagtca   1373
tcctaaggcg cataaccatt tataaaaatc atccttcatt ctattttacc ctatcatcct   1433
ctgcaagaca gtcctccctc aaacccacaa gccttctgtc ctcacagtcc cctgggccat   1493
ggtaggagag acttgcttcc ttgttttccc ctcctcagca agccctcata gtccttttta   1553
agggtgacag gtcttacagt catatatcct ttgattcaat tccctgagaa tcaaccaaag   1613 caaattttc aaaagaagaa acctgctata aagagaatca ttcattgcaa catgatataa    1673
aataacaaca caataaaagc aattaaataa acaaacaata gggaaatgtt taagttcatc   1733
atggtactta gacttaatgg aatgtcatgc cttatttaca tttttaaaca ggtactgagg   1793
gactcctgtc tgccaagggc cgtattgagt actttccaca acctaattta atccacacta   1853
tactgtgaga ttaaaaacat tcattaaaat gttgcaaagg ttctataaag ctgagagaca   1913
aatatattct ataactcagc aatcccactt ctaggatcc                         1952

<210> SEQ ID NO 2
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Glu Lys Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Glu Ser
        35                  40                  45

Val Asp Asn Tyr Gly Ile Ser Phe Met Asn Trp Phe Gln Gln Lys Pro
    50                  55                  60
```

```
Gly Lys Ala Pro Lys Leu Leu Ile Tyr Ala Ala Ser Asn Gln Gly Ser
 65                  70                  75                  80

Gly Val Pro Ser Arg Phe Ser Gly Ser Gly Ser Gly Thr Asp Phe Thr
                 85                  90                  95

Leu Thr Ile Ser Ser Leu Gln Pro Asp Asp Phe Ala Thr Tyr Tyr Cys
            100                 105                 110

Gln Gln Ser Lys Glu Val Pro Trp Thr Phe Gly Gln Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 3
<211> LENGTH: 3246
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (12)..(416)
<220> FEATURE:
<221> NAME/KEY: CDS
<222> LOCATION: (660)..(953)
<220> FEATURE:
<221> NAME/KEY: CDS
<222> LOCATION: (1345)..(1389)
<220> FEATURE:
<221> NAME/KEY: CDS
<222> LOCATION: (1508)..(1837)
<220> FEATURE:
<221> NAME/KEY: CDS
<222> LOCATION: (1935)..(2255)

<400> SEQUENCE: 3
tctagaccac c atg gga tgg agc tgg atc ttt ctc ttc ctc ctg tca gga        50
           Met Gly Trp Ser Trp Ile Phe Leu Phe Leu Leu Ser Gly
             1               5                  10 act gct ggc gtc cac tct cag gtt cag ctg gtg cag tct gga gct gag        98
Thr Ala Gly Val His Ser Gln Val Gln Leu Val Gln Ser Gly Ala Glu
         15                  20                  25 gtg aag aag cct ggg agc tca gtg aag gtt tcc tgc aaa gct tct ggc       146
Val Lys Lys Pro Gly Ser Ser Val Lys Val Ser Cys Lys Ala Ser Gly
 30                  35                  40                  45 tac acc ttc act gac tac aac atg cac tgg gtg agg cag gct cct ggc       194
Tyr Thr Phe Thr Asp Tyr Asn Met His Trp Val Arg Gln Ala Pro Gly
                 50                  55                  60 caa ggc ctg gaa tgg att gga tat att tat cct tac aat ggt ggt acc       242
Gln Gly Leu Glu Trp Ile Gly Tyr Ile Tyr Pro Tyr Asn Gly Gly Thr
             65                  70                  75
```

```
ggc tac aac cag aag ttc aag agc aag gcc aca att aca gca gac gag      290
Gly Tyr Asn Gln Lys Phe Lys Ser Lys Ala Thr Ile Thr Ala Asp Glu
            80                  85                  90 agt act aac aca gcc tac atg gaa ctc tcc agc ctg agg tct gag gac      338
Ser Thr Asn Thr Ala Tyr Met Glu Leu Ser Ser Leu Arg Ser Glu Asp
    95                 100                 105 act gca gtc tat tac tgc gca aga ggg cgc ccc gct atg gac tac tgg      386
Thr Ala Val Tyr Tyr Cys Ala Arg Gly Arg Pro Ala Met Asp Tyr Trp
110                 115                 120                 125 ggc caa ggg act ctg gtc act gtc tct tca ggtaagaatg ccctctagac        436
Gly Gln Gly Thr Leu Val Thr Val Ser Ser
                130                 135 caccatggga tggagctttc tggggcaggc caggcctgac cttggctttg gggcagggag    496
ggggctaagg tgaggcaggt ggcgccagcc aggtgcacac ccaatgccca tgagcccaga    556
cactggacgc tgaacctcgc ggacagttaa gaacccaggg gcctctgcgc cctgggccca    616
gctctgtccc acaccgcggt cacatggcac cacctctctt gca gcc tcc acc aag      671
                                             Ala Ser Thr Lys ggc cca tcg gtc ttc ccc ctg gca ccc tcc tcc aag agc acc tct ggg      719
Gly Pro Ser Val Phe Pro Leu Ala Pro Ser Ser Lys Ser Thr Ser Gly
140                 145                 150                 155 ggc aca gcg gcc ctg ggc tgc ctg gtc aag gac tac ttc ccc gaa ccg      767
Gly Thr Ala Ala Leu Gly Cys Leu Val Lys Asp Tyr Phe Pro Glu Pro
                160                 165                 170 gtg acg gtg tcg tgg aac tca ggc gcc ctg acc agc ggc gtg cac acc      815
Val Thr Val Ser Trp Asn Ser Gly Ala Leu Thr Ser Gly Val His Thr
                    175                 180                 185 ttc ccg gct gtc cta cag tcc tca gga ctc tac tcc ctc agc agc gtg      863
Phe Pro Ala Val Leu Gln Ser Ser Gly Leu Tyr Ser Leu Ser Ser Val
                190                 195                 200 gtg acc gtg ccc tcc agc agc ttg ggc acc cag acc tac atc tgc aac      911
Val Thr Val Pro Ser Ser Ser Leu Gly Thr Gln Thr Tyr Ile Cys Asn
205                 210                 215 gtg aat cac aag ccc agc aac acc aag gtg gac aag aaa gtt              953
Val Asn His Lys Pro Ser Asn Thr Lys Val Asp Lys Lys Val
220             225                 230 ggtgagaggc cagcacaggg agggaggtg tctgctggaa gccaggctca gcgctcctgc    1013
ctggacgcat cccggctatg cagccccagt ccagggcagc aaggcaggcc ccgtctgcct   1073
cttcacccgg aggcctctgc ccgccccact catgctcagg gagagggtct tctggctttt   1133
tccccaggct ctgggcaggc acaggctagg tgccctaac ccaggccctg cacacaaagg    1193
ggcaggtgct gggctcagac ctgccaagag ccatatccgg gaggaccctg cccctgacct   1253
aagcccaccc caaaggccaa actctccact ccctcagctc ggacaccttc tctcctccca   1313
gattccagta actcccaatc ttctctctgc a gag ccc aaa tct tgt gac aaa      1365
                                   Glu Pro Lys Ser Cys Asp Lys
                                               235                 240 act cac aca tgc cca ccg tgc cca ggtaagccag cccaggcctc gccctccagc    1419
Thr His Thr Cys Pro Pro Cys Pro
                245 tcaaggcggg acaggtgccc tagagtagcc tgcatccagg acaggcccc agccgggtgc    1479 tgacacgtcc acctccatct cttcctca gca cct gaa ctc ctg ggg gga ccg      1531
                                Ala Pro Glu Leu Leu Gly Gly Pro
                                            250                 255 tca gtc ttc ctc ttc ccc cca aaa ccc aag gac acc ctc atg atc tcc     1579
Ser Val Phe Leu Phe Pro Pro Lys Pro Lys Asp Thr Leu Met Ile Ser
            260                 265                 270
```

```
cgg acc cct gag gtc aca tgc gtg gtg gtg gac gtg agc cac gaa gac        1627
Arg Thr Pro Glu Val Thr Cys Val Val Val Asp Val Ser His Glu Asp
        275                 280                 285 cct gag gtc aag ttc aac tgg tac gtg gac ggc gtg gag gtg cat aat        1675
Pro Glu Val Lys Phe Asn Trp Tyr Val Asp Gly Val Glu Val His Asn
        290                 295                 300 gcc aag aca aag ccg cgg gag gag cag tac aac agc acg tac cgt gtg        1723
Ala Lys Thr Lys Pro Arg Glu Glu Gln Tyr Asn Ser Thr Tyr Arg Val
305                 310                 315                 320 gtc agc gtc ctc acc gtc ctg cac cag gac tgg ctg aat ggc aag gag        1771
Val Ser Val Leu Thr Val Leu His Gln Asp Trp Leu Asn Gly Lys Glu
                325                 330                 335 tac aag tgc aag gtc tcc aac aaa gcc ctc cca gcc ccc atc gag aaa        1819
Tyr Lys Cys Lys Val Ser Asn Lys Ala Leu Pro Ala Pro Ile Glu Lys
            340                 345                 350 acc atc tcc aaa gcc aaa ggtgggaccc gtggggtgcg agggccacat               1867
Thr Ile Ser Lys Ala Lys
                355 ggacagaggc cggctcggcc caccctctgc cctgagagtg accgctgtac caacctctgt      1927 ccctaca ggg cag ccc cga gaa cca cag gtg tac acc ctg ccc cca tcc        1976
        Gly Gln Pro Arg Glu Pro Gln Val Tyr Thr Leu Pro Pro Ser
            360                 365                 370 cgg gat gag ctg acc aag aac cag gtc agc ctg acc tgc ctg gtc aaa        2024
Arg Asp Glu Leu Thr Lys Asn Gln Val Ser Leu Thr Cys Leu Val Lys
        375                 380                 385 ggc ttc tat ccc agc gac atc gcc gtg gag tgg gag agc aat ggg cag        2072
Gly Phe Tyr Pro Ser Asp Ile Ala Val Glu Trp Glu Ser Asn Gly Gln
        390                 395                 400 ccg gag aac aac tac aag acc acg cct ccc gtg ctg gac tcc gac ggc        2120
Pro Glu Asn Asn Tyr Lys Thr Thr Pro Pro Val Leu Asp Ser Asp Gly
405                 410                 415                 420 tcc ttc ttc ctc tac agc aag ctc acc gtg gac aag agc agg tgg cag        2168
Ser Phe Phe Leu Tyr Ser Lys Leu Thr Val Asp Lys Ser Arg Trp Gln
                425                 430                 435 cag ggg aac gtc ttc tca tgc tcc gtg atg cat gag gct ctg cac aac        2216
Gln Gly Asn Val Phe Ser Cys Ser Val Met His Glu Ala Leu His Asn
            440                 445                 450 cac tac acg cag aag agc ctc tcc ctg tct ccg ggt aaa tgagtgcgac         2265
His Tyr Thr Gln Lys Ser Leu Ser Leu Ser Pro Gly Lys
        455                 460                 465 ggccggcaag cccccgctcc ccgggctctc gcggtcgcac gaggatgctt ggcacgtacc      2325
ccctgtacat acttcccggg cgcccagcat ggaaataaag cacccagcgc tgccctgggc      2385
ccctgcgaga ctgtgatggt tctttccacg ggtcaggccg agtctgaggc ctgagtggca     2445
tgagggaggc agagcgggtc ccactgtccc cacactggcc caggctgtgc aggtgtgcct     2505
gggccgccta gggtggggct cagccagggg ctgccctcgg cagggtgggg gatttgccag     2565
cgtggccctc cctccagcag cacctgccct gggctgggcc acgggaagcc ctaggagccc    2625 ctgggacag acacacagcc cctgcctctg taggagactg tcctgttctg tgagcgccct      2685
gtcctccgac ctccatgccc actcgggggc atgcctagtc catgtgcgta gggacaggcc    2745
ctccctcacc catctacccc cacggcacta acccctggct gccctgccca gcctcgcacc   2805
cgcatgggga cacaaccgac tccggggaca tgcactctcg ggccctgtgg agggactggt    2865
gcagatgccc acacacacac tcagcccaga cccgttcaac aaaccccgca ctgaggttgg    2925
ccggccacac ggccaccaca cacacacgtg cacgcctcac acacggagcc tcacccgggc    2985
```

```
gaactgcaca gcacccagac cagagcaagg tcctcgcaca cgtgaacact cctcggacac    3045
aggcccccac gagccccacg cggcacctca aggcccacga gcctctcggc agcttctcca    3105
catgctgacc tgctcagaca aacccagccc tcctctcaca agggtgcccc tgcagccgcc    3165
acacacacac aggggatcac acaccacgtc acgtccctgg ccctggccca cttcccagtg    3225
ccgcccttcc ctgcaggatc c                                              3246
```

<210> SEQ ID NO 4
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Gly Trp Ser Trp Ile Phe Leu Phe Leu Ser Gly Thr Ala Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Asn Met His Trp Val Arg Gln Ala Pro Gly Gln Gly Leu
    50                  55                  60

Glu Trp Ile Gly Tyr Ile Tyr Pro Tyr Asn Gly Thr Gly Tyr Asn
65                  70                  75                  80

Gln Lys Phe Lys Ser Lys Ala Thr Ile Thr Ala Asp Glu Ser Thr Asn
                85                  90                  95

Thr Ala Tyr Met Glu Leu Ser Ser Leu Arg Ser Glu Asp Thr Ala Val
            100                 105                 110

Tyr Tyr Cys Ala Arg Gly Arg Pro Ala Met Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
```

```
305                 310                 315                 320
Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
                355                 360                 365

Leu Pro Pro Ser Arg Asp Glu Leu Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
        450                 455                 460

Lys
465
```

LOW DOSE ANTIBODY-BASED METHODS FOR TREATING HEMATOLOGIC MALIGNANCIES

This application is a § 371 national stage entry of PCT Application No. PCT/US2017/034406, filed May 25, 2017, which claims priority of U.S. Provisional Application No. 62/342,568, filed May 27, 2016, the contents of which are incorporated herein by reference in their entirety.

Sequence Listing

The instant application contains a Sequence Listing which has been filed electronically in ASCII format and is hereby incorporated by reference in its entirety. Said ASCII copy, created on Apr. 1, 2019, is named Actinium-1PUS_SL.txt and is 22,419 bytes in size.

Throughout this application, various publications are cited. The disclosure of these publications is hereby incorporated by reference into this application to describe more fully the state of the art to which this invention pertains.

FIELD OF THE INVENTION

The present invention relates to treating a subject afflicted with a hematologic malignancy using a low dose of a potent agent (such as a toxin-conjugated antibody) targeting a hematologic malignancy-associated antigen, wherein the subject has a low peripheral cancerous cell burden.

BACKGROUND OF THE INVENTION

Cytotoxic agent-conjugated antibodies have recently become a promising tool for treating hematologic malignancies such as acute myeloid leukemia ("AML"). Of particular interest are therapeutic conjugates of cancer cell-specific antibodies with potent cytotoxic agents like alpha-emitting isotopes such as 225-actinium ($^{225}$Ac).

However, doses of monoclonal antibodies labeled with potent cytotoxic agents cannot safely be escalated above maximum tolerated doses established in clinical trials. This safety-based dosing constraint prevents the escalation of antibody conjugate doses to saturation levels.

Therefore, for these conjugates, there is an unmet need for treating AML and other hematologic cancers by administering them in doses low enough to avoid toxicity while high enough to be therapeutically effective. There is also an unmet need to achieve this balance in a manner independent of patient age, co-morbidities and disease severity.

SUMMARY OF THE INVENTION

This invention provides a method for treating a subject afflicted with a hematologic malignancy comprising administering to the subject an agent targeting a hematologic malignancy-associated antigen, wherein the subject has a low peripheral cancerous cell burden.

This invention also provides a method for treating a subject afflicted with a hematologic malignancy and having a high peripheral cancerous cell burden, comprising (i) medically lowering the subject's peripheral cancerous cell burden, and (ii) while the subject's peripheral cancerous cell burden is still low, administering to the subject an agent targeting a hematologic malignancy-associated antigen.

This invention further provides a method for treating a human subject afflicted with acute myeloid leukemia comprising administering to the subject an anti-CD33 antibody labeled with an alpha-emitting isotope, wherein (i) the subject has a low peripheral blast burden, and (ii) the antibody is administered in sub-saturating dose.

This invention still further provides a method for treating a human subject afflicted with acute myeloid leukemia and having a high peripheral blast burden, comprising (i) medically lowering the subject's peripheral blast burden, and (ii) while the subject's peripheral blast burden is still low, administering to the subject an anti-CD33 antibody labeled with an alpha-emitting isotope, wherein the antibody is administered in a sub-saturating dose.

This invention still further provides a method for treating a human subject afflicted with acute myeloid leukemia comprising intravenously administering $^{225}$Ac-labeled HuM195 to the subject, wherein (i) the subject has a low peripheral blast burden, and (ii) the $^{225}$Ac-labeled HuM195 is administered in a sub-saturating dose.

Finally, this invention provides a method for treating a human subject afflicted with acute myeloid leukemia and having a high peripheral blast burden, comprising (i) medically lowering the subject's peripheral blast burden, and (ii) while the subject's peripheral blast burden is still low, intravenously administering $^{225}$Ac-labeled HuM195 to the subject, wherein the $^{225}$Ac-labeled HuM195 is administered in a sub-saturating dose.

BRIEF DESCRIPTION OF THE FIGURES

FIG. 2
This figure shows the complete sequence of the HuM195 light chain gene cloned in pVk between the XbaI and BamHI sites. The nucleotide number indicates its position in the plasmid pVk-HuM195. The VL and CK exons are translated in single letter code; the dot indicates the translation termination codon. The mature light chain begins at the double-underlined aspartic acid (D). The intron sequence is in italics. The polyA signal is underlined.

FIG. 3
This figure shows the complete sequence of the HuM195 heavy chain gene cloned in pVg1 between the XbaI and BamHI sites. The nucleotide number indicates its position in the plasmid pVg1-HuM195. The VH, CH1, H, CH2 and CH3 exons are translated in single letter code; the dot indicates the translation termination codon. The mature heavy chain begins at the double-underlined glutamine (Q). The intron sequences are in italics. The polyA signal is underlined.

FIG. 6
This figure shows a dosing protocol for $^{225}$Ac-Lintuzumab ($^{225}$Ac-HuM195) treatment of AML.

DETAILED DESCRIPTION OF THE INVENTION

Figure 1:
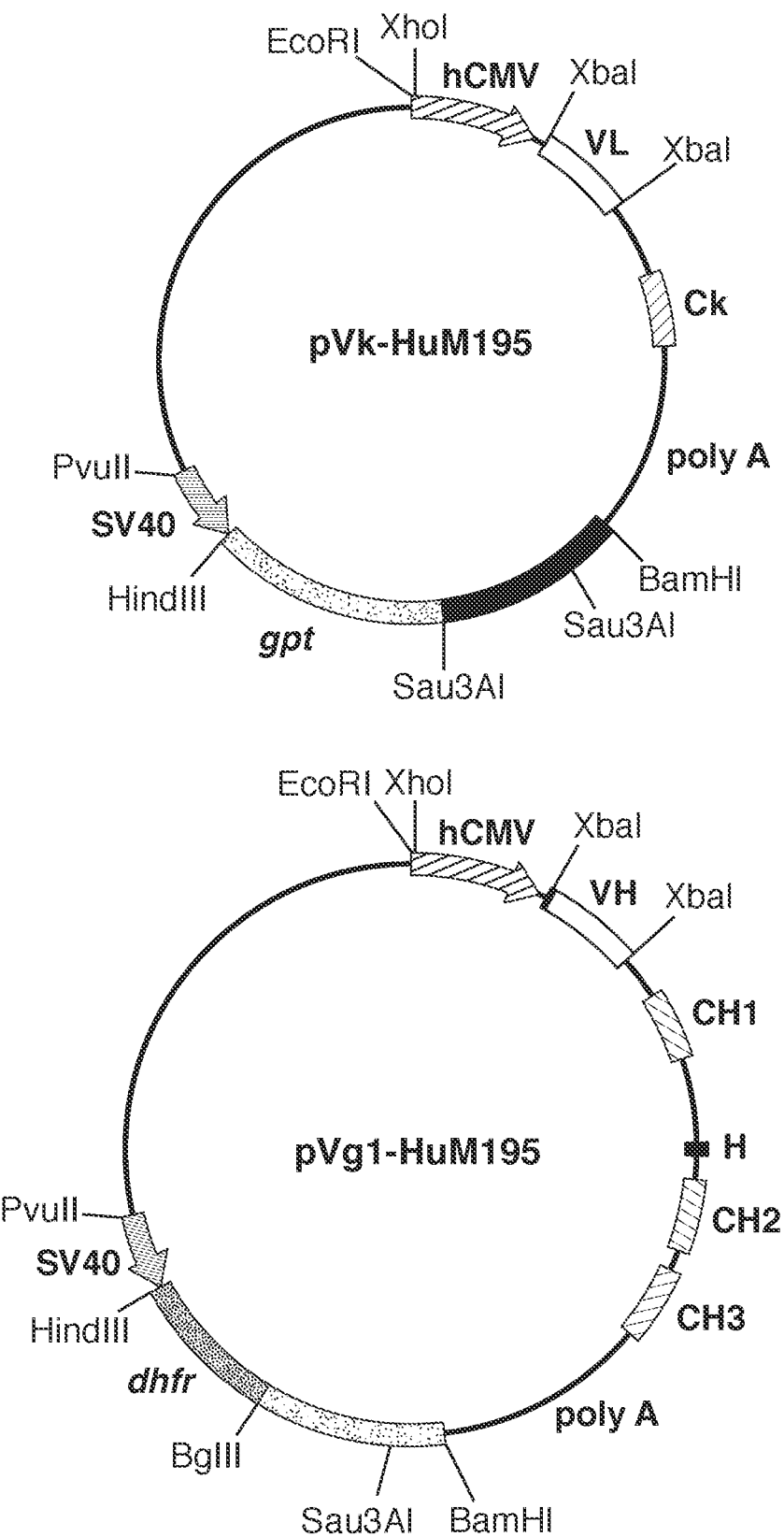
FIG. 1
This figure shows a schematic diagram of the expression plasmids for HuM195. The humanized VL and VH exons of HuM195 are flanked by XbaI sites. The VL exon was inserted into mammalian expression vector pVk, and the VH exon into pVg1 (Co, et al., J. Immunol. 148:1149-1154, 1992).

This invention provides surprisingly effective methods for treating a subject afflicted with a hematologic malignancy, such as AML. These methods use a potent agent, such as an antibody conjugated with an alpha-emitting isotope, targeting a hematologic malignancy-associated antigen, such as CD33. The subject who is being treated has a low peripheral cancerous cell burden and, ideally, only a sub-saturating dose of agent is needed to treat the subject.

Definitions

In this application, certain terms are used which shall have the meanings set forth as follows.

As used herein, "administer", with respect to an agent, means to deliver the agent to a subject's body via any known method. Specific modes of administration include, without limitation, intravenous, oral, sublingual, transdermal, subcutaneous, intraperitoneal, intrathecal and intra-tumoral administration.

In addition, in this invention, the various antibodies and other antigen-targeting agents used can be formulated using one or more routinely used pharmaceutically acceptable carriers. Such carriers are well known to those skilled in the art. For example, injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

As used herein, the "agent" targeting a hematologic malignancy-associated antigen can be any type of compound or composition useful for such purpose. Types of agents include, without limitation, antibodies, other protein-based drugs, peptides, nucleic acids, carbohydrates and small molecules drugs.

As used herein, the term "antibody" includes, without limitation, (a) an immunoglobulin molecule comprising two heavy chains and two light chains and which recognizes an antigen; (b) polyclonal and monoclonal immunoglobulin molecules; (c) monovalent and divalent fragments thereof, and (d) bi-specific forms thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies, and fragments thereof. Antibodies may be human, humanized or nonhuman.

As used herein, an "anti-CD33 antibody" is an antibody that binds to any available epitope of CD33. In one embodiment, the anti-CD33 antibody binds to the epitope recognized by the antibody HuM195.

As used herein, the term "burden", when used in connection with a cancerous cell, means quantity. So, a cancerous cell "burden" means the quantity of cancerous cells. Cancerous cells have a burden with respect to their tissue of origin (i.e., the primary site of disease), such as the "bone marrow blast burden" in the case of AML. Cancerous cells also have a burden with respect to one or more tissues other than those of origin, such as the blast burden in blood, liver and spleen in the case of AML. The term "peripheral burden" relates to such cells. The peripheral burden of cancerous cells, such as blasts in the case of AML, can be measured in different ways with different outcomes. For example, in the case of AML, the "peripheral blast burden" can be measured as the total blast population outside of the bone marrow, or the total blast population of the blood, spleen and liver combined, or simply the blast population of the blood as measured in cells per unit volume. As used herein in connection with AML and other cancers originating in the bone marrow, and unless stated otherwise, the term "peripheral cancerous cell burden" (e.g., peripheral blast burden) refers to the cancerous cell population of the blood as measured in cells per unit volume (e.g., cells/µl). This blood-based measurement is a useful proxy for the more cumbersome measurements of spleen and liver burdens, for example.

Herein, a peripheral cancerous cell burden in a subject is "high" if, when the subject is administered an agent (e.g., an antibody) targeting a hematologic malignancy-associated antigen at the maximum safe dose, the agent does not reach the primary site of disease in a sufficient amount to bind to more than 90% of its target antigens at that site. Conversely, a peripheral cancerous cell burden in a subject is "low" if, when the subject is administered an agent (e.g., an antibody) targeting a hematologic malignancy-associated antigen at the maximum safe dose, the agent reaches the primary site of disease in a sufficient amount to bind to more than 90% of its target antigens at that site. In the case of AML, examples of low peripheral blast burden are those yielding blood blast burdens at or below 1,000 blast cells/µl, at or below 500 blast cells/µl, at or below 400 blast cells/µl, at or below 300 blast cells/µl, at or below 200 blast cells/µl, at or below 100 blast cells/µl, and at or below 50 blast cells/µl.

As used herein, the term "cytotoxic agent" includes, without limitation, a radionuclide, a protein-based toxin, a non-protein based toxin, and a chemotherapeutic agent. Radionuclides include, for example, alpha-emitting isotopes (i.e., alpha-emitting isotopes, such as $^{225}$Ac, $^{213}$Bi and $^{213}$Po), beta-emitting isotopes (e.g., $^{90}$Y), and gamma-emitting isotopes (e.g., $^{137}$Cs (which emits gamma rays via its decay product $^{137}$Ba)). Protein-based toxins include, without limitation, ricin and toxic portions thereof, and botulinum toxin and toxic portions thereof. Methods for affixing a cytotoxic agent to an antibody (i.e., "labeling" an antibody with a cytotoxic agent) are well known.

A "hematologic malignancy", also known as a blood cancer, is a cancer that originates in blood-forming tissue, such as the bone marrow or other cells of the immune system. Hematologic malignancies include, without limitation, leukemias (such as AML, acute promyelocytic leukemia, acute lymphoblastic leukemia, acute mixed lineage leukemia, chronic myeloid leukemia, chronic lymphocytic leukemia, hairy cell leukemia, large granular lymphocytic leukemia), myelodysplastic syndrome (MDS), myeloproliferative disorders (polycitermia vera, essential thrombocytosis, primary myelofibrosis and chronic myeloid leukemia), lymphomas, multiple myeloma, and MGUS and similar disorders.

As used herein, a "hematologic malignancy-associated antigen" can be, for example, a protein and/or carbohydrate marker found exclusively or predominantly on the surface of a cancer cell associated with that particular malignancy. Examples of hematologic malignancy-associated antigens include, without limitation, CD20, CD33, CD38, CD45, CD52, CD123 and CD319.

The antibody "HuM195" (also known as lintuzumab) is known, as are methods of making it. Likewise, methods of labeling HuM195 with $^{225}$Ac are known. These methods are exemplified, for example, in Scheinberg, et al., U.S. Pat. No. 6,683,162. This information is also exemplified in the examples and figures below.

A low peripheral cancerous cell burden can be "medically induced" using any known method for doing so. These methods include, for example, pharmaceutical induction (such as by oral administration of hydroxyurea at 10-70 mg/kg/day), and spleen removal.

As used herein, the term "subject" includes, without limitation, a mammal such as a human, a non-human primate, a dog, a cat, a horse, a sheep, a goat, a cow, a rabbit, a pig, a rat and a mouse. Where the subject is human, the subject can be of any age. For example, the subject can be 60 years or older, 65 or older, 70 or older, 75 or older, 80 or older, 85 or older, or 90 or older. For a human subject afflicted with AML, the subject's bone marrow blast burden can be, for example, over 5%, over 10%, over 20%, over 30%, over 40%, over 50%, over 60%, over 70%, over 80%, or over 90%. As an additional example, for a human subject afflicted with AML, the subject can be newly diagnosed, or relapsed and/or refractory, or in remission.

As used herein, a "sub-saturating dose" of an agent targeting a hematologic malignancy-associated antigen is one that introduces into the subject's body fewer target antigen-binding sites (e.g., Fab's) than there are target antigens. By way of example, for an anti-CD33 antibody, a sub-saturating dose is one that introduces into the subject's body fewer CD33-binding sites than there are CD33 molecules. In one embodiment, a sub-saturating dose of an agent targeting a hematologic malignancy-associated antigen is one where the ratio of target antigen-binding sites to target antigens is less than or equal to 9:10. In another embodiment, the ratio of target antigen-binding sites to target antigens is less than or equal to 1:2, less than or equal to 1:5, less than or equal to 1:10, less than or equal to 1:20, or less than or equal to 1:100.

For an agent such as an antibody labeled with an alpha-emitting isotope or other cytotoxic agent, the majority of the drug administered to a subject typically consists of non-labeled antibody, with the minority being the labeled antibody.

Thus, in one embodiment, a sub-saturating dose of an agent targeting a hematologic malignancy-associated antigen is one where the ratio of total (i.e., labeled and unlabeled) target antigen-binding sites to target antigens is less than or equal to 9:10 (and can be less than or equal to 1:2, less than or equal to 1:5, less than or equal to 1:10, less than or equal to 1:20, or less than or equal to 1:100). In another embodiment, a sub-saturating dose of an agent targeting a hematologic malignancy-associated antigen is one where the ratio of labeled target antigen-binding sites to target antigens is less than or equal to 9:10 (and can be less than or equal to 1:2, less than or equal to 1:5, less than or equal to 1:10, less than or equal to 1:20, or less than or equal to 1:100).

Sub-saturating doses used in connection with this invention include, for example, a single administration, and two or more administrations (i.e., fractions). The amount administered in each dose can be measured, for example, by radiation (e.g., μCi/kg) or weight (e.g., mg/kg or mg/m$^2$). In the case of $^{225}$Ac-HuM195 (also known as "Actimab-A") for treating AML, dosing regimens include the following, without limitation: (i) 2×0.5 μCi/kg, 2×1.0 μCi/kg, 2×1.5 μCi/kg, or 2×2.0 μCi/kg, where the fractions are administered one week apart; (ii) 1×0.5 μCi/kg, 1×1.0 μCi/kg, 1×2.0 μCi/kg, 1×3.0 μCi/kg, or 1×4.0 μCi/kg; (iii) 1×15-20 μg/kg (0.03-0.06 μg/kg labeled); and (iv) less than or equal to approximately 2 mg per subject (approximately 0.04 mg labeled antibody per subject).

As used herein, "treating" a subject afflicted with a disorder shall include, without limitation, (i) slowing, stopping or reversing the disorder's progression, (ii) slowing, stopping or reversing the progression of the disorder's symptoms, (iii) reducing the likelihood of the disorder's recurrence, and/or (iv) reducing the likelihood that the disorder's symptoms will recur. In the preferred embodiment, treating a subject afflicted with a disorder means (i) reversing the disorder's progression, ideally to the point of eliminating the disorder, and/or (ii) reversing the progression of the disorder's symptoms, ideally to the point of eliminating the symptoms and/or (iii) reducing or eliminating the likelihood of relapse (i.e. consolidation, which is a common goal of post remission therapy for AML and, ideally, results in the destruction of any remaining leukemia cells).

The treatment of hematologic malignancy, such as the treatment of AML, can be measured according to a number of clinical endpoints. These include, without limitation, survival time (such as weeks, months or years of improved survival time, e.g., one, two or more months of additional survival time), and response status (such as complete remission (CR), near complete remission (nCR), very good partial remission (VGPR) and partial remission (PR)).

In one embodiment, treatment of hematologic malignancy, such as the treatment of AML, can be measured in terms of remission. Included here are the following non-limiting examples. (1) Morphologic complete remission ("CR"): ANC≥1,000/mcl, platelet count≥100,000/mcl, <5% bone marrow blasts, no Auer rods, no evidence of extramedullary disease. (No requirements for marrow cellularity, hemoglobin concentration). (2) Morphologic complete remission with incomplete blood count recovery ("CRi"): Same as CR but ANC may be <1,000/mcl and/or platelet count<100,000/mcl. (3) Partial remission (PR): ANC≥1,000/mcl, platelet count>100,000/mcl, and at least a 50% decrease in the percentage of marrow aspirate blasts to 5-25%, or marrow blasts<5% with persistent Auer rods. These criteria and others are known, and are described, for example, in SWOG Oncology Research Professional (ORP) Manual Volume I, Chapter 11A, Leukemia (2014).

Embodiments of the Invention

This invention provides a first method for treating a subject afflicted with a hematologic malignancy comprising administering to the subject an agent targeting a hematologic malignancy-associated antigen, wherein the subject has a low peripheral cancerous cell burden.

In one embodiment of the first method, the subject's low peripheral cancerous cell burden is medically induced, such as by administering a pharmaceutical agent like hydroxyurea. Alternatively, the subject's low peripheral cancerous cell burden can be naturally occurring.

This invention also provides a second method for treating a subject afflicted with a hematologic malignancy and having a high peripheral cancerous cell burden, comprising (i) medically lowering the subject's peripheral cancerous cell burden, and (ii) while the subject's peripheral cancerous cell burden is still low, administering to the subject an agent targeting a hematologic malignancy-associated antigen.

Preferably, in these methods, the subject is human. In one embodiment of these methods, the hematologic malignancy is acute myeloid leukemia, and the cancerous cells are leukemic blasts.

The antigen-targeting agent is preferably administered in a sub-saturating dose, and can be administered intravenously or via another route. This agent can be, for example, an anti-CD33 antibody labeled with a cytotoxic agent (e.g., an alpha-emitting isotope like $^{225}$Ac).

This invention further provides a third method for treating a human subject afflicted with acute myeloid leukemia comprising administering to the subject an anti-CD33 antibody labeled with an alpha-emitting isotope, wherein (i) the subject has a low peripheral blast burden, and (ii) the antibody is administered in a sub-saturating dose.

In one embodiment, the subject's low peripheral blast burden is medically induced, and is preferably pharmaceutically induced (e.g., via administering hydroxyurea). Alternatively, the subject's low peripheral blast burden can be naturally occurring.

This invention still further provides a fourth method for treating a human subject afflicted with acute myeloid leukemia and having a high peripheral blast burden, comprising (i) medically lowering the subject's peripheral blast burden, and (ii) while the subject's peripheral blast burden is still low, administering to the subject an anti-CD33 antibody labeled with an alpha-emitting isotope, wherein the antibody is administered in a sub-saturating dose.

Preferably, medically lowering the subject's peripheral blast burden comprises pharmaceutically lowering the subject's peripheral blast burden (e.g., via administering hydroxyurea). The antibody can be administered intravenously or via another route.

This invention still further provides a method for treating a human subject afflicted with acute myeloid leukemia comprising intravenously administering $^{225}$Ac-labeled HuM195 to the subject, wherein (i) the subject has a low peripheral blast burden, and (ii) the $^{225}$Ac-labeled HuM195 is administered in a sub-saturating dose.

In one embodiment, the subject's low peripheral blast burden is medically induced, and is preferably pharmaceutically induced (e.g., via administering hydroxyurea). Alternatively, the subject's low peripheral cancerous cell burden can be naturally occurring. The $^{225}$Ac-labeled HuM195 is preferably administered intravenously.

Finally, this invention provides a method for treating a human subject afflicted with acute myeloid leukemia and having a high peripheral blast burden, comprising (i) medically lowering the subject's peripheral blast burden, and (ii) while the subject's peripheral blast burden is still low, intravenously administering $^{225}$Ac-labeled HuM195 to the subject, wherein the $^{225}$Ac-labeled HuM195 is administered in a sub-saturating dose.

Preferably, medically lowering the subject's peripheral blast burden comprises pharmaceutically lowering the subject's peripheral blast burden (e.g., via administering hydroxyurea). Also, the $^{225}$Ac-labeled HuM195 is preferably administered intravenously.

This invention will be better understood by reference to the examples which follow, but those skilled in the art will readily appreciate that the specific examples detailed are only illustrative of the invention as described more fully in the claims which follow thereafter.

EXAMPLES

Example 1—Structure of $^{225}$Ac-Lintuzumab ($^{225}$Ac-HuM195)

Figure 4:
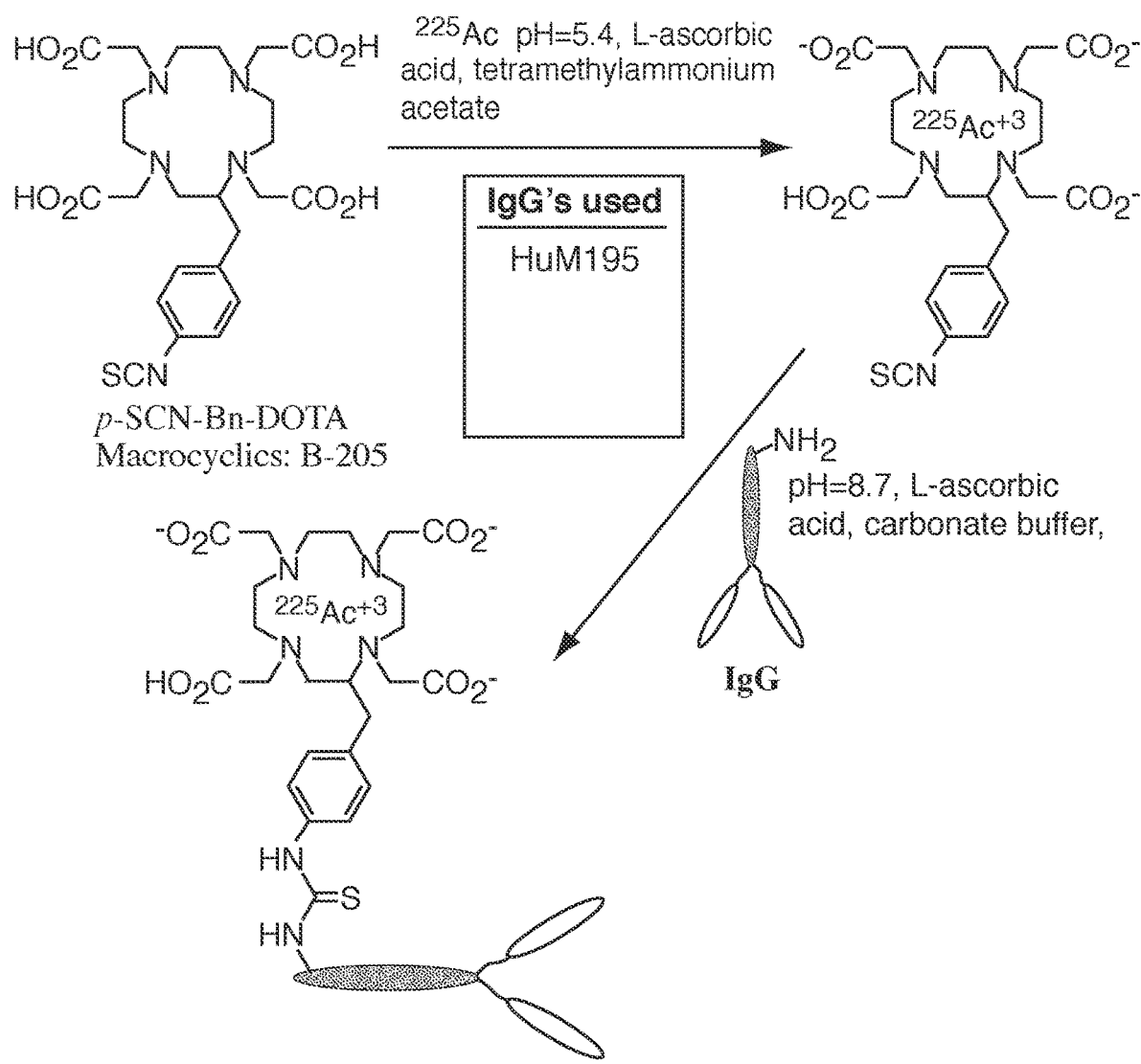
FIG. 4
This figure shows the structure of $^{225}$Ac-Lintuzumab ($^{225}$Ac-HuM195).

$^{225}$Ac-Lintuzumab includes three key components; humanized monoclonal antibody HuM195 (generic name, lintuzumab), the alpha-emitting radioisotope $^{225}$Ac, and the bi-functional chelate 2-(p-isothiocyanatobenzyl)-1,4,7,10-tetraazacyclododecane-1,4,7,10-tetraacetic acid (p-SCN-Bn-DOTA). As depicted in FIG. 4, HuM195 is radiolabeled using the bi-functional chelate p-SCN-Bn-DOTA that binds to $^{225}$Ac and that is covalently attached to the IgG via a lysine residue on the antibody.

Example 2—p-SCN-Bn-DOTA

DOTA, 2-(4-Isothiocyanatobenzyl)-1,4,7,10-tetraazacyclododecane tetraacetic acid (Macrocyclics item code B205-GMP) is synthesized by a multi-step organic synthesis that is fully described in U.S. Pat. No. 4,923,985.

Example 3—Preparation of $^{225}$Ac-Lintuzumab ($^{225}$Ac-HuM195)

The procedure for preparing $^{225}$Ac-Lintuzumab is based on the method described by Michael R. McDevitt, "Design and synthesis of $^{225}$Ac radioimmunopharmaceuticals", Applied Radiation and Isotope, 57 (2002), 841-847. The procedure involves radiolabeling the bi-functional chelate, p-SCN-Bn-DOTA, with the radioisotope $^{225}$Ac, followed by binding of the radiolabeled p-SCN-Bn-DOTA to the antibody (HuM195). The construct, $^{225}$Ac-p-SCN-Bn-DOTA-HuM195, is purified using 10 DG size exclusion chromatography and eluted with 1% human serum albumin (HSA). The resulting drug product, Ac225-Lintuzumab, is then passed through a 0.2 μm sterilizing filter.

Example 4—Process Flow for Preparation of $^{225}$Ac-Lintuzumab ($^{225}$Ac-HuM195)

Figure 5:
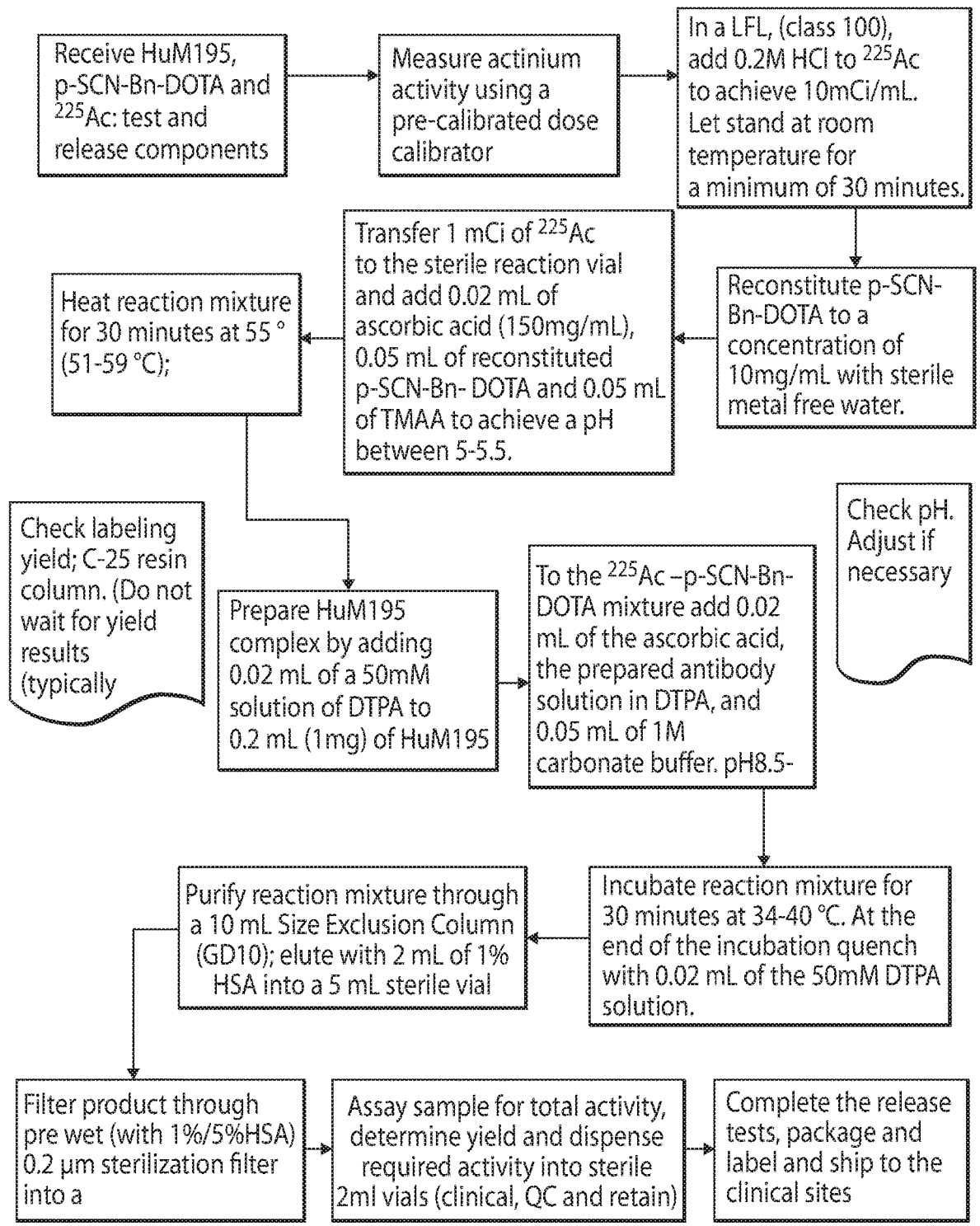
FIG. 5
This figure shows a flowchart for the production of $^{225}$Ac-HuM195.

The procedure, shown in FIG. 5, begins with confirming the identity of all components and the subsequent QC release of the components to production. The $^{225}$Ac is assayed to confirm the level of activity and is reconstituted to the desired activity concentration with hydrochloric acid. A vial of lyophilized p-SCNBn-DOTA is reconstituted with metal-free water to a concentration of 10 mg/mL. To the actinium reaction vial, 0.02 ml of ascorbic acid solution (150 mg/mL) and 0.05 ml of reconstituted p-SCN-Bn-DOTA are added and the pH adjusted to between 5 and 5.5 with 2M tetramethylammonium acetate (TMAA). The mixture is then heated at 55±4° C. for 30 minutes.

To determine the labeling efficiency of the $^{225}$Ac-p-SCN-Bn-DOTA, an aliquot of the reaction mixture is removed and applied to a 1 ml column of Sephadex C25 cation exchange resin. The product is eluted in 24 ml fractions with a 0.9% saline solution. The fraction of $^{225}$Ac activity that elutes is $^{225}$Ac-p-SCN-Bn-DOTA and the fraction that is retained on the column is un-chelated, unreactive $^{225}$Ac. Typically, the labeling efficiency is greater than 95%.

To the reaction mixture, 0.22 ml of previously prepared HuM195 in DTPA (1 mg HuM195) and 0.02 ml of ascorbic acid are added. The DTPA is added to bind any trace amounts of metals that may compete with the labeling of the antibody. The ascorbic acid is added as a radio-protectant. The pH is adjusted with carbonate buffer to pH 8.5-9. The mixture is heated at 37±3 OC for 30 minutes. The final product is purified by size exclusion chromatography using 10DG resin and eluted with 2 ml of 1% HSA. Typical reaction yields are 10%.

Example 5—Actimab-A Treatment in a Phase 1 Clinical Trial for Relapsed and Refractory AML Patients Relapsed and refractory adult AML patients of all ages were enrolled in this single treatment group trial. Treatment consisted of a single infusion of Actimab-A administered at escalating doses as shown in Table 1 below.

TABLE 1

| Dose Level | $^{225}$Ac Activity | HuM195 Dose |
|---|---|---|
| 1 | 0.5 μCi/kg | 15 μg/kg |
| 2 | 1 μCi/kg | 15 μg/kg |
| 3 | 2 μCi/kg | 20 μg/kg |
| 4 | 4 μCi/kg | 25 μg/kg |
| 5 | 3 μCi/kg | 20 μg/kg |

Each cohort was planned for three patients. Dose escalation proceeded if none of the three patients experienced dose-limiting toxicities (DLTs). If one of the three patients experienced DLTs, the cohort was expanded with additional three patients. If none experienced DLTs, the dose escalation continued. If two out of six patients experienced DLTs, dose level was decreased. The total of 20 patients were treated and their baseline characteristics were collected, including circulating blasts counts. Circulating blasts counts were available for 18 patients. After the treatment, patients were followed up for safety and efficacy, including anti-leukemic effects, which primarily comprises blasts as a percentage of all cells in patients' red bone marrow.

Example 6—Actimab-A Treatment in a Phase 1/2 Trial in Newly Diagnosed AML Patients In the Phase 1 portion of the Actimab-A Phase 1/2 multicenter trial, newly diagnosed older AML patients ineligible for treatment with intensive chemotherapy regimens were treated with a course of low dose cytarabine followed by escalating fractionated doses (two fractions) of Actimab-A per Table 2 below. If the patient's disease did not progress after treatment with Actimab-A, and if the patient remained otherwise eligible, additional up to 11 low dose cytarabine cycles of treatment were to be administered.

TABLE 2

| Dose Level | Ac-225 Activity per fractionated dose (μCi/Kg) | Total Dose (μCi/Kg) | HuM195 per fractionated dose (μg/Kg) | Total HuM195 dose (μg/Kg) |
|---|---|---|---|---|
| 1 | 0.5 | 1.0 | 7.5 | 15 |
| 2 | 1 | 2 | 10 | 20 |
| 3 | 1.5 | 3 | 10 | 20 |
| 4 | 2 | 4 | 12.5 | 25 |

Each cohort was planned to enroll 3 patients. Dose escalation proceeded if none of the three patients experienced dose-limiting toxicities ("DLTs"). If one of the three patients experienced DLTs, the cohort was expanded with an additional three patients. If none experienced DLTs, the dose escalation continued. If two out of six patients experienced DLTs, the dose level was decreased. A total of 18 patients were treated and their baseline characteristics were collected, including circulating blast counts. Circulating blast counts were available for all 18 patients. After the treatment, patients were followed up for safety and efficacy, including anti-leukemic effects primarily comprising blasts as a percentage of all cells in patients' red bone marrow.

Example 7—Efficacy Outcomes in an Actimab-A Phase 1 Trial for Relapsed and Refractory AML Patients and a Phase 1/2 Trial for Older Newly Diagnosed AML Patients Initial anti-leukemic efficacy was analyzed as a function of achieving a composite complete response ("CRc"), where CRc is defined as achieving a post-treatment patient bone marrow blast percentage of ≤5%. Response rates per dose level in both referenced trials are shown in Tables 3 and 4 below. Table 3 shows efficacy outcomes for the Phase 1 single dose trial in relapsed and refractory AML patients.

TABLE 3

| Patients in the Trial | | | |
|---|---|---|---|
| | Patients Treated | Achieved CRc | % CRc |
| Dose level 1 (0.5 μCi/kg) | 3 | 0 | 0% |
| Dose level 2 (1.0 μCi/kg) | 3 | 1 | 33% |
| Dose level 3 (2.0 μCi/kg) | 5 | 0 | 0% |
| Dose level 4 (3.0 μCi/kg) | 5 | 1 | 20% |
| Dose level 5 (4.0 μCi/kg) | 2 | 1 | 50% |

Table 4 shows efficacy outcomes for the Phase 1 fractionated dose trial in older newly diagnosed AML patients.

TABLE 4

| Patients in the Trial | | | |
|---|---|---|---|
| | Patients Treated | Achieved CRc | % CRc |
| Dose level 1 (0.5 μCi/kg × 2) | 3 | 0 | 0% |
| Dose level 2 (1.0 μCi/kg × 2) | 6 | 1 | 17% |
| Dose level 3 (1.5 μCi/kg × 2) | 3 | 2 | 67% |
| Dose level 4 (2.0 μCi/kg × 2) | 6 | 2 | 33% |
| Total | 18 | 5 | 28% |

Example 8—Efficacy Analysis by Commonly Used Risk Factors of an Actimab-A Phase 1/2 Trial for Newly Diagnosed AML Patients There are several commonly used metrics used as prognostic factors to determine the likelihood of response in newly diagnosed AML. The most commonly used prognostic factors are age, cytogenetics and the presence of antecedent hematologic disease (most often myelodysplastic syndrome (MDS, in which case AML is referred to as secondary AML ("sAML")). Those factors were applied to analyze efficacy outcomes in the Phase 1 older newly diagnosed AML trial. Results of those analyses are presented in Table 5 below.

TABLE 5

| | Responders | Non-responders |
|---|---|---|
| Age (Median) | 76 | 77 |
| | Genetic risk | |
| | High | Intermediate |
| Response % | 29% | 27% |
| | De novo vs sAML | |
| | De novo | sAML |
| Response % | 50% | 17% |

It was concluded that none of the above commonly used prognostic factors correlates with statistically significant differences in response outcomes.

Example 9—Peripheral Blast Burden Correlation with Efficacy Outcomes in Actimab-A Phase 1 and Phase 1/2 Clinical Trials for AML Patients Additional analyses were performed, and it was surprisingly discovered that the number of circulating blasts has a strong and statistically significant correlation with the clinical outcome. This discovery was observed in both trials, i.e., in both relapsed/refractory and newly diagnosed patients. A circulating blast count of fewer than 200 per microliter corresponded with responses. However, when the circulating blast count was greater than or equal to 200 per microliter, no patients responded. These data are presented in Table 6 below.

TABLE 6

| Circulating blasts per microliter | ≥200 | <200 |
|---|---|---|
| Phase 1 single dose trial | 0% | 43% |
| Phase 1/2 fractionated dosing trial | 0% | 42% |

Example 10—Responses in Newly Diagnosed and Relapsed/Refractory AML Patients According to Peripheral Blast Status Prior to Actimab-A Treatment Response outcomes in AML patients were compared by dose level in the two referenced trials by selecting only patients with <200 circulating blasts per microliter of peripheral blood. Tables 7-9 below summarize these findings.

Table 7 shows efficacy outcomes per peripheral blast counts by dose level in the Phase 1 trial for relapsed and refractory AML patients.

TABLE 7

|  | Pts pb ≥ 200 | Pts with CRc | % CRc | Pts pb < 200 | Pts with CRc | % CRc |
|---|---|---|---|---|---|---|
| Dose level 1 (0.5 µCi/kg) | 2 | 0 | 0% | 1 | 0 | 0% |
| Dose level 2 (1 µCi/kg) | 0 | 0 | 0% | 3 | 1 | 33% |
| Dose level 3 (2 µCi/kg) | 5 | 0 | 0% | 0 | 0 | NA |
| Dose level 4 (3 µCi/kg) | 3 | 0 | 0% | 2 | 1 | 50% |
| Dose level 5 (4 µCi/kg) | 1 | 0 | 0% | 1 | 1 | 100% |
| Total | 11 | 0 | 0% | 7 | 3 | 43% |

Table 8 shows efficacy outcomes per peripheral blast counts by dose level in the Phase 1/2 trial for newly diagnosed older AML patients.

TABLE 8

|  | Pts pb ≥ 200 | Pts with CRc | % CRc | Pts pb < 200 | Pts with CRc | % CRc |
|---|---|---|---|---|---|---|
| Dose level 1 (0.5 µCi/kg × 2) | 1 | 0 | 0% | 2 | 0 | 0% |
| Dose level 2 (1 µCi/kg × 2) | 3 | 0 | 0% | 3 | 1 | 33% |
| Dose level 3 (1.5 µCi/kg × 2) | 0 | 0 | 0% | 3 | 2 | 67% |
| Dose level 4 (2 µCi/kg × 2) | 2 | 0 | 0% | 4 | 2 | 50% |
| Total | 6 | 0 | 0% | 12 | 5 | 42% |

Table 9 shows a statistical analysis of the responses in both AML trials.

TABLE 9

| Patients with: | CRc rates | CRc % |
|---|---|---|
| <200 pb | 8/19 | 42% |
| ≥200 pb | 0/17 | 0% |

*p value: 0.002416 (highly significant)

Example 11—Anti-Leukemic Effect of Actimab-A Based on Significant Leukemic Blast Cell Killing In early stage clinical trials, anti-leukemic effect is often measure as the ability of the studied therapy to reduce leukemic blast burden in the bone marrow by ≥50%. The ability of Actimab-A to have this effect was analyzed by comparing patients with peripheral blast burdens of ≥200 and patients with peripheral blast burdens of <200 per microliter of peripheral blood. Results of these analyses are presented in Table 10 below. These results represent analyses of 38 patients wherein data were available for 31 of them.

TABLE 10

|  | ≥50% reduced patients (%) | <50% reduced patients (%) |
|---|---|---|
| pb < 200 | 12 (80%) | 3 (20%) |
| pb ≥ 200 | 4 (25%) | 12 (75%) |

*p value: 0.002197 (highly significant)

REFERENCES

1. Burnett, et al., "A Comparison of Low-Dose Cytarabine and Hydroxyurea With or Without All-trans Retinoic Acid for Acute Myeloid Leukemia and High-Risk Myelodysplastic Syndrome in Patients Not Considered Fit for Intensive Treatment", Cancer, Mar. 15, 2007, Vol. 109, No 6.
2. Co, et al., J. Immunol. 148:1149-1154, 1992.
3. Domino and Baldor, "The 5-Minute Clinical Consult 2014."
4. Gansow, et al., U.S. Pat. No. 4,923,985.
5. Harousseau, et al., "A randomized phase 3 study of tipifamib compared with best supportive care, including hydroxyurea, in the treatment of newly diagnosed acute myeloid leukemia in patients 70 years or older", Blood, 6 Aug. 2009, Vol. 114, No. 6.
6. Jurcic, et al., "Phase I Trial of Targeted Alpha-Particle Therapy with Actinium-225 ($^{225}$Ac)-Lintuzumab and Low-Dose Cytarabine (LDAC) in Patients Age 60 or Older with Untreated Acute Myeloid Leukemia (AML)", ASH 2016 Abstract.
7. Kumar, "Genetic Abnormalities and Challenges in the Treatment of Acute Myeloid Leukemia", Genes & Cancer 2(2):95-107, 2011.

8. McDevitt, "Design and synthesis of [225]Ac radioimmunopharmaceuticals", Applied Radiation and Isotope, 57 (2002), 841-847.
9. Mulford et al., "The Promise of Targeted α-Particle Therapy", The Journal of Nuclear Medicine, Vol. 46, No. 1 (Suppl), January 2005.
10. Mylotarg Wyeth Product Monograph (2005).
11. Pollard, et al., "Correlation of CD33 expression level with disease characteristics and response to gemtuzumab ozogamicin containing chemotherapy in childhood AML", Blood, 2012, Apr. 19, 119(16):3705-3711.
12. V. H. J. van der Velden, et al., "High CD33-antigen loads in peripheral blood limit the efficacy of gemtuzumab ozogamicin (Mylotarg) treatment in acute myeloid leukemia patients", Leukemia, 2004, May, 18(5):983-8.
13. Scheinberg, et al., U.S. Pat. No. 6,683,162.
14. SWOG Oncology Research Professional (ORP) Manual, Volume I, Chapter 11A, Leukemia (2014).

What is claimed is:

1. A method for treating a human subject afflicted with acute myeloid leukemia comprising intravenously administering to the subject $^{225}$Ac-labeled HuM195, wherein (a) the subject has a peripheral blast burden below 200 blast cells/µl, and (b) the $^{225}$Ac-labeled HuM195 is administered at a dose of (i) 2×1.0 µCi/kg, 2×1.5 µCi/kg, or 2×2.0 µCi/kg, wherein the fractions are administered one week apart; or (ii) 1×1.0 µCi/kg, 1×2.0 µCi/kg, 1×3.0 µCi/kg, or 1×4.0 µCi/kg.

2. The method of claim 1, wherein the $^{225}$Ac-labeled HuM195 is administered at a dose of 2×1.0 µCi/kg, 2×1.5 µCi/kg, or 2×2.0 µCi/kg, wherein the fractions are administered one week apart.

3. The method of claim 1, wherein the $^{225}$Ac-labeled HuM195 is administered at a dose of 1×1.0 µCi/kg, 1×2.0 µCi/kg, 1×3.0 µCi/kg, or 1×4.0 µCi/kg.

4. A method for treating a human subject afflicted with acute myeloid leukemia and having a peripheral blast burden at or above 200 blast cells/µl, comprising (a) medically lowering the subject's peripheral blast burden to below 200 blast cells/µl, and (b) while the subject's peripheral blast burden is still below 200 blast cells/µl, intravenously administering to the subject $^{225}$Ac-labeled HuM195 at a dose of (i) 2×1.0 µCi/kg, 2×1.5 µCi/kg, or 2×2.0 µCi/kg, wherein the fractions are administered one week apart; or (ii) 1×1.0 µCi/kg, 1×2.0 µCi/kg, 1×3.0 µCi/kg, or 1×4.0 µCi/kg.

5. The method of claim 4, wherein the $^{225}$Ac-labeled HuM195 is administered at a dose of 2×1.0 µCi/kg, 2×1.5 µCi/kg, or 2×2.0 µCi/kg, wherein the fractions are administered one week apart.

6. The method of claim 4, wherein the $^{225}$Ac-labeled HuM195 is administered at a dose of 1×1.0 µCi/kg, 1×2.0 µCi/kg, 1×3.0 µCi/kg, or 1×4.0 µCi/kg.

* * * * *